United States Patent [19]

Engelbach et al.

[11] 4,036,860

[45] July 19, 1977

[54] PRODUCTION OF ANTHRAQUINONE

[75] Inventors: Heinz Engelbach, Limburgerhof; Michael Jolyon Sprague, Mannheim, both of Germany

[73] Assignee: BASF Aktiengesellschaft, Ludwigshafen, Germany

[21] Appl. No.: 607,356

[22] Filed: Aug. 25, 1975

[30] Foreign Application Priority Data

Sept. 7, 1974 Germany ............................. 2442911

[51] Int. Cl.² .............................................. C09B 1/00
[52] U.S. Cl. ................................................... 260/369
[58] Field of Search ........................................ 260/369

[56] References Cited

U.S. PATENT DOCUMENTS 3,872,134 3/1975 Wistuba et al. ...................... 260/369

FOREIGN PATENT DOCUMENTS 2,050,798 4/1972 Germany ...................... 260/369 UX

*Primary Examiner*—Paul F. Shaver
*Attorney, Agent, or Firm*—Keil, Thompson & Shurtleff

[57] ABSTRACT

Anthraquinone is produced by oxidation of diphenylmethane compounds in the gaseous phase in the presence of oxygen-containing compounds of vanadium and titanium and at least one other metal in a specific ratio by weight. Anthraquinone prepared by the process of the invention is a starting material for the production of dyes and pesticides.

13 Claims, No Drawings

PRODUCTION OF ANTHRAQUINONE

The invention relates to a process for the production of anthraquinone by the oxidation of a diphenylmethane compound in the gaseous phase in the presence of an oxygen-containing compound of vanadium and of titanium and of at least one other metal in specified proportions by weight.

German Laid-Open Specification (DOS) No. 2,050,798 (patent application No. P 20 50 798.6) relates process for the production of anthraquinone by the oxidation of a diphenylmethane derivative of the formula:

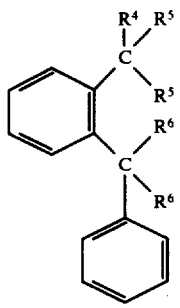

(Ia)

in which $R^4$, $R^5$ and $R^6$ are identical or different and each is hydrogen or an aliphatic radical, moreover the two radicals $R^5$ and/or the two radicals $R^6$ may together form an oxo group, and/or $R^4$ and one radical $R^6$ may together form an aliphatic radical with substituted methylene or with at least two carbon atoms or (when the radicals $R^5$ form an oxo group) may be unsubstituted methylene or both radicals $R^5$ and one radical $R^6$ or one radical $R^5$ and both radicals $R^6$ or both radicals $R^5$ and both radicals $R^6$ may together be an aliphatic radical, with oxygen in the gaseous phase in the presence of a compound of pentavalent vanadium as a catalyst.

All the Examples described vanadium pentoxide as a component of a pentavalent vanadium catalyst which contains antimony as a second metal. Titanium and certain proportions of titanium dioxide and vanadium pentoxide were not set out as specific catalysts for diphenylmethane bearing an aliphatic radical as a substituent in the 2-position on one ring and corresponding diphenyl methanes bearing aliphatic radicals as substituents on the methylene group. All the Examples disclosed bicyclic compounds in the form of indene derivatives, indanone derivatives and naphthalene derivatives. The catalysts used were advantageously applied to a carrier by a flame spraying or plasma spraying method; such an application gives layers having very small internal surfaces or none at all. When a diphenylmethane bearing an aliphatic radical as a substituent on one ring in the 2-position or a corresponding diphenylmethane bearing an aliphatic radical as a substituent on the methylene group was oxidized with the antimony/pentavalent vanadium catalyst described in the Examples (this not being disclosed in the Laid-Open Specification) yields of up to 52% of theory were obtained.

It is an object of this invention to provide a novel process for producing anthraquinone in a simpler and more economical manner and in a higher yield and purity, particularly in relation to byproducts which are insoluble in water and alkalies.

We have found that anthraquinone is advantageously prepared by oxidation of a diphenylmethane derivative in the gaseous phase in the presence of a compound of pentavalent vanadium as catalyst at elevated temperature by oxidizing a diphenylmethane compound of the formula:

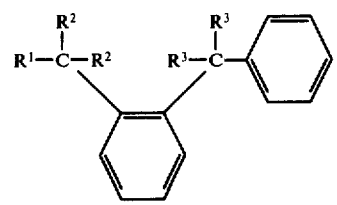

(I)

In which $R^1$, $R^2$ and $R^3$ are identical or different and each is hydrogen or an aliphatic radical, in the presence of:

a. an oxygen-containing compound of vanadium in an amount (calculated as vanadium pentoxide) of from 1 to 70% by weight;

b. an oxygen-containing compound of titanium in an amount (calculated at titanium dioxide) of from 29 to 95% by weight; and c. an oxygen-containing compound of one or more of the metals tellurium, caesium, thallium and antimony in an amount in each case (calculated as metal oxide) of from 0.01 to 20% by weight, based on the oxygen-containing compounds and calculated as the total amount of metal oxide.

When using 2-methyldiphenylmethane the reaction may be represented by the following equation:

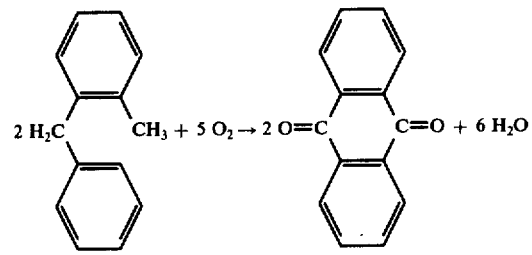

As compared with the prior art the process of the invention surprisingly gives in a simpler and more economical manner better yields of anthraquinone of better purity, particularly as regards by-products which are insoluble in water and alkalies. Oxides of vanadium and titanium and the other metals in the said proportions prove to be catalysts of high selectivity for the oxidation of the said diphenylmethane in the manufacture of anthraquinone. Byproducts formed besides anthraquinone in the process according to the invention are as a rule volatile or of good solubility in alkalies; for example an anthraquinone having a purity of more than 99.0 % is generally obtained by an alkaline washing of the reaction products condensed from the reaction gas. All these advantageous results are surprising because it was to be assumed from the prior art that large amounts of oxidation products and decomposition products would be formed and the yield of anthraquinone thereby impaired. Similarly having regard to German Laid-Open Specification (DOS) No. 2,050,798 it was not to be expected that this specific catalysis of the oxidation of alkyldiphenylmethanes would be caused by a catalyst which in addition to vandium contains only titanium and the abovementioned additioned metals in substantially larger amounts and advantageously has a fairly large internal surface.

The starting materials (I) may be prepared by known methods. For example 2-benzyltoluene may be prepared by the reaction of benzyl chloride and toluene (Ber. 6 (1873), 906 ). Homologs of the said starting materials bearing substituents on the methylene group can be obtained in an analogous manner, for example by the reaction of toluene with appropriately substituted styrenes. Preferred starting materials (I) are those in whose formula $R^1$, $R^2$ and $R^3$ are identical or different and each is hydrogen or alkyl of one to four and particularly one, two or three carbon atoms. The said radicals may bear one or more groups and/or atoms which are inert under the reaction conditions, for example alkoxy or alkyl of one to three carbon atoms, as substituents.

The following compounds are examples of starting materials (I): 2-butyldiphenylmethane, 2-(methoxyethyl)-diphenylmethane, 2 -(ethoxymethyl) -diphenylmethane, 2-isopropyldiphenylmethane, 2-isobutyldiphenylmethane, 2-tert.-butyldiphenylmethane, 2-propyldiphenylmethane, 2-ethyldiphenylmethane, 2-sec.-butyldiphenylmethane and preferably 2-methyldiphenylmethane or homologs bearing as substituents on the methylene group one or two identical or different methoxyethyl, ethoxymethyl, methyl, ethyl, isopropyl, n-butyl, isobutyl, sec.-butyl or propyl groups.

The oxidation is carried out as a rule with an excess of oxygen. Oxygen is generally used in the form of air but any mixtures of oxygen and gases which are inert under the reaction condition, such as argon, water vapor, nitrogen and/or carbon dioxide or flue gas may be used. The loading, particularly in the case of 2 -methyldiphenylmethane, may be from 5 to 100 grams, advantageously from 10 to 60 grams and particularly from 25 to 55 grams of starting material (I) per cubic meter (STP) of air. It is convenient to use from 20 to 2000 grams, advantageously from 50 to 500 grams and particularly from 100 to 350 grams of starting material (I) per liter of catalyst (or supported catalyst) per hour. As a rule the same amount of starting material (I) based on 1 liter of catalyst (supported catalyst) is used in batchwise operation.

The oxygen-containing compounds of the said metals are advantageously vanadium pentoxide, vandates and/or oxides of the metals specified under (b) and (c). The vanadates may be mono- or polyvanadates and particularly orthovandates, pyrovanadates or metavandates. Other oxygen-containing compounds of the said metals, for example carbonates such as caesium carbonate, are however also suitable. Salts of the said metals with oxyacids formed from the said metals such as tellurium may also be used; for example caesium tellurate is suitable. Catalysts which contain oxygen-containing compounds of vanadium and titanium and one or two of the other metals are preferred. Vanadium may optionally be present only in the form of vanadates of the metals specified under (b) and (c).

Independently of the actual constitution of any particular compound and of the composition of the mixture of oxygen-containing compounds, the oxygen-containing compounds are calculated in the case of the vanadium compounds as vanadium pentoxide and in the case of the metals under (b) and (c) as the following metal oxides: (b) titanium (IV) oxide ($TiO_2$); (c) tellurium (VI) oxide ($TeO_3$); caesium oxide ($Cs_2O$); thallium (I) oxide ($Tl_2O$), antimony (III) oxide ($Sb_2O_3$). Calculation of the metal oxide embraces all the compounds present containing the metal in question and is thus independent of whether this metal is present in only one compound or in more than one compound; thus vanadium may be present in more than one compound, for example simultaneously as $V_2O_5$ and $SbVO_4$ in the mixture, or one of the other metals may be present in more than one compound, for example caesium simultaneously as caesium oxide and caesium vanadate, and is calculated as one weight of $V_2O_5$ or $Cs_2O$. $SbVO_4$ is thus calculated as $V_2O_5$ and $Sb_2O_3$ in equivalent amounts. References in % by weight of the metal oxide concerned thus relate to the total amount of all oxygen-containing compounds which is calculated as the total amount of all the metal oxides.

Compounds may also be used which form oxygen-containing compounds and particularly oxides or vandates of the said metals in the production of the catalyst or during the reaction. Examples of such compounds are hydroxides, oxyacids, oxides of lower valency or salts such as carbonates, bicarbonates or nitrates of the said metals. These include the following: caesium hydroxide, telluric acid, caesium carbonate, caesium nitrate, thallium acetate, vanadyl oxalate, caesium formate, thallium hydroxide, antimony chloride, titanic acid, titanyl sulfate, titanium(II) oxide, titanium (IV) chloride, vanadyl formate, vanadic acid, vanadyl nitrate, vanadyl acetate, vanadyl tartrate, vandium oxychloride, vandyl citrate, ammonium vanadate and vanadium (IV) oxide. The titanium dioxide may be present in the form of rutile or preferably in the form of anatase. It may be used in anhydrous form or in the form of hydrates $TiO_2 \cdot xH_2O$, for example as orthotitanic acid or metatitanic acid.

The reaction is preferably carried out in the presence of oxygen-containing compounds of:

a. vanadium, calculated as vanadium(V) oxide, in an amount of from 5 to 66% by weight;
b. titanium, calculated as titanium dioxide, in an amount of from 40 to 90% by weight; and
c. one or more of the metals tellurium, caesium, thallium and antimony, calculated as metal oxide, in an amount of from 0.1 to 10% by weight in the case of antimony and tellurium, in the case of thallium of from 0.1 to 5% by weight and in the case of caesium in an amount of from 0.1 to 5% weight, based on the oxygen-containing compounds and calculated as the total amount of metal oxide.

The internal surface area of the catalyst is advantageously from 1 to 80 and preferably from 2 to 25 square meters per gram of catalyst. In the case of metal oxides such as titanium dioxide particle sizes of from 0.1 to 1.5 and preferably from 0.2 to 0.5 micron are conveniently chosen. The catalysts may optionally be used together with a carrier material, for example pumice, silicon carbide, silicon oxides, aluminum oxides and advantageously steatite. Convenient amounts are from 0.5 to 30 and preferably from 0.8 to 12% by weight of catalyst based on the carrier and convenient layer thicknesses of catalyst are from 0.02 to 2 millimeters on the carrier.

The shape and size of the catalyst may be chosen within a wide range; it is advantageous to use globular, pelleted or lumpy catalysts or extrudates having a mean diameter of from 2 to 12 millimeters.

The oxidation is as a rule carried out at a temperature of from 200° to 450° C and preferably from 300° to 420° C at atmospheric or superatmospheric pressure, batchwise or preferably continuously. The reaction temperature is measured as the temperature of the salt bath (nitrate melt) which heats the wall of the reaction tube and is referred to hereinafter as the tube wall temperature. The starting material (I) may be oxidized as follows: the starting diphenylmethane compound is vaporized in a current of air heated to more than 150° C. It is also possible to saturate a portion of the reaction off-gas which is devoid of oxygen with the vapor of the starting material and thus to set up the desired concentration of starting material (I) in the reaction mixture. The mixture of gas and vapor is then passed through the bed of catalyst in a reactor at the reaction temperature. Convenient reactors are tubular reactors cooled with a salt bath, fluidization reactors with inbuilt cooling units or layered reactors with intermediate cooling. The end product is the separated from the reaction mixture by a conventional method. For example the gas leaving the reactor is passed through one or more than one separator. The anthraquinone may then if desired be freed from byproducts by washing with water or an alkaline solution. The end product may also be separated by passing the gaseous reaction mixture into water or into an alkaline solution so that the anthraquinone is obtained as an insoluble solid having high purity.

If necessary, the end product may be purified, for example by dissolving it in an alkaline solution of sodium dithionite and filtering off unreacted starting material. Then the end product may be precipitated from the filtrate by air oxidation and separated. Similarly the reaction mixture may be passed into water or dilute caustic soda solution and the end products may be isolated from the resulting solid residue by sublimation. The said purification operations are possible but not as a rule necessary because byproducts which are insoluble in alkalies are generally not present in appreciable amounts.

Anthraquinone prepared by the process of the invention is a valuable starting material for the manufacture of dyes and pesticides. The abovementioned publications and Ullmanns Encyklopaedie der technischen Chemie, volume 3, pages 659 et seq., may be referred to for details of uses.

The following Examples illustrate the invention. The parts specified in the Examples are part by weight. They bear the same relation to parts by volume as the kilogram to the liter.

EXAMPLES 1 to 20 a. Production of the catalyst

Vanadium pentoxide (1 part) is dissolved in 8 parts of water with an addition of 2.5 parts of oxalic acid and to this solution which has been heated to 60° C the metal compounds and anatase are added. The suspension thus obtained is stirred and sprayed with propellant gas onto a heated rotated carrier (steatite spheres having a diameter of 6 mm and a rough surface). The carrier thus coated is dried for 16 hours at 110° C and then calcined for 16 hours at 500° C. The following Table gives the composition of each catalyst and the percentage of catalyst (active material) in the whole supported catalyst (active material plus carrier).

b. Oxidation 62 parts of the supported catalyst prepared under (a) is charged into a tubular reactor (internal diameter 21 mm). A mixture of 100,000 parts by volume of air and the amount (in parts) of o-methyldiphenylmethane given in the Table is passed through the catalyst per hour. The tube wall temperatures and the reaction conditions are included in the Table. The gaseous reaction mixture leaving the reactor is cooled to 50° C so that the end product and unreacted starting material are condensed. The uncondensed portion is washed with water. After evaporation of the wash water the residue which remains is united with the condensate. The yields of anthraquinone are given in % of theory based on reacted starting material (I) in the Table and are determined in the crude end product by ultraviolet absorption. Fluorenone and xanthone in the end product are determined by gas chromatography.

The columns in the Table have the following meanings:

A = Example No;
B = the composition of the catalyst in % by weight;
C = amount of catalyst (in parts) per 100 parts of the whole supported catalyst;
D = the tube wall temperature in ° C;
E = the amount of starting material (I) in parts;
F = the loading in grams of starting material (I) per cubic meter (STP) of air;
G = the loading in grams of starting material (I) per liter of catalyst per hour;
H = the yield of anthraquinone in parts;
I = the yield of anthraquinone of % of theory;
J = the content in % by weight of fluorenone and xanthone in the end material.

TABLE

| A | B | C | D | E | F | G | H | I | J |
|---|---|---|---|---|---|---|---|---|---|
| 1 | 49.5 $V_2O_5$/50.0 $TiO_2$/0.5 TlNO3 | 2.30 | 415 | 19.8 | 40 | 80 | 13.8 | 61 | 0.2 |
| 2 | 16.4 $V_2O_5$/83.4 $TiO_2$/0.2 TlNO3 | 2.60 | 420 | 20.9 | 42 | 84 | 13.5 | 57 | 0.3 |
| 3 | 49.0 $V_2O_5$/50.0 $TiO_2$/1.0 TlNO3 | 2.19 | 420 | 21.1 | 42 | 84 | 14.7 | 61 | 0.15 |
| 4 | 16.4 $V_2O_5$/83.3 $TiO_2$/0.3 TlNO3 | 2.31 | 450 | 20.1 | 40 | 80 | 12.2 | 53 | 0.4 |
| 5 | 47.5 $V_2O_5$/50.0 $TiO_2$/2.5 TlNO3 | 2.12 | 440 | 17.6 | 35 | 70 | 10.7 | 53 | 1.7 |
| 6 | 15.9 $V_2O_5$/83.3 $TiO_2$/0.8 TlNO3 | 2.34 | 420 | 19.9 | 40 | 80 | 13.4 | 59 | 0.05 |
| 7 | 63.4 $V_2O_5$/33.3 $TiO_2$/3.3 $Sb_2O_3$ | 6.24 | 370 | 20.5 | 41 | 82 | 13.5 | 57 | 0.3 |
| 8 | 47.5 $V_2O_5$/50.0 $TiO_2$/2.5 $Sb_2O_3$ | 1.80 | 405 | 17.9 | 36 | 72 | 12.1 | 59 | <0.05 |
| 9 | 47.5 $V_2O_5$/50.0 $TiO_2$/2.5 $Sb_2O_3$ | 2.61 | 400 | 21.6 | 43 | 86 | 14.3 | 58 | <0.05 |
| 10 | 47.5 $V_2O_5$/50.0 $TiO_2$/2.5 $Sb_2O_3$ | 6.89 | 370 | 20.3 | 41 | 81 | 13.1 | 56 | 0.25 |
| 11 | 23.8 $V_2O_5$/75.0 $TiO_2$/1.2 $Sb_2O_3$ | 5.80 | 360 | 21.4 | 43 | 86 | 13.7 | 56 | 0.5 |
|   |   | 5.80 | 370 | 21.1 | 42 | 84 | 13.5 | 56 | 0.25 |
| 12 | 49.0 $V_2O_5$/50.0 $TiO_2$ 0.5 $Sb_2O_3$/0.5 TlNO3 | 2.12 | 420 | 21.2 | 42 | 85 | 14.4 | 60 | <0.05 |
| 13 | 16.3 $V_2O_5$/83.3 $TiO_2$ 0.2 $Sb_2O_3$/0.2 TlNO3 | 2.43 | 410 | 17.8 | 36 | 71 | 12.2 | 60 | <0.05 |
| 14 | 48.0 $V_2O_5$/50.0 $TiO_2$ 1.0 $Sb_2O_3$/1.0 TiO2 | 2.23 | 420 | 19.1 | 38 | 76 | 14.0 | 64 | 0.2 |
| 15 | 16.1 $V_2O_5$/83.3 $TiO_2$ 0.3 $Sb_2O_3$/0.3 TlNO3 | 2.27 | 400 | 21.9 | 44 | 88 | 15.3 | 61 | <0.05 |
| 16 | 45.0 $V_2O_5$/50.0 $TiO_2$ |   |   |   |   |   |   |   |   |

TABLE-continued

| A | B | C | D | E | F | G | H | I | J |
|---|---|---|---|---|---|---|---|---|---|
|  | 2.5 Sb₂O₃/2.5 TlNO3 | 2.09 | 420 | 21.9 | 44 | 88 | 16.0 | 64 | 0.4 |
| 17 | 15.0 V₂O₅/83.4 TiO2  0.8 Sb₂O₃/0.8 TlNO3 | 2.49 | 425 | 20.5 | 41 | 82 | 13.7 | 58 | 0.8 |
| 18 | 62.7 V₂O₅/33.3 TiO2  3.3 Sb₂O₃/0.6 H₆TeO6 | 6.59 | 385 | 21.0 | 42 | 84 | 13.9 | 58 | 0.2 |
| 19 | 47.0 V₂O₅/50.0 TiO2  2.5 Sb₂O₃/0.5 H₆TeO6 | 9.55 | 375 | 21.7 | 43 | 87 | 14.3 | 58 | 0.15 |
| 20 | 48.0 V₂O₅150.0 TiO2  1.0 CsNO₃/1.0 H₆TeO6 | 8.76 | 420 | 21.3 | 43 | 85 | 13.8 | 57 | 0.8 |

What we claim is:

1. A process for the production of anthraquinone by the oxidation of a diphenylmethane derivative with oxygen in the gaseous phase in the presence of a pentavalent vanadium compound as a catalyst at elevated temperature which comprises oxidizing a diphenylmethane compound of the formula (I):

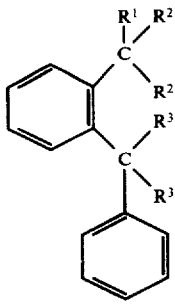

in which $R^1$, $R^2$ and $R^3$ are identical or different and each is hydrogen or an aliphatic radical, in the presence of oxygen-containing compounds of
  a. vanadium in an amount, calculated as vanadium pentoxide, of from 1 to 70% by weight;
  b. titanium in an amount, calculated as titanium dioxide, of from 29 to 95% by weight; and
  c. one or more of the metals tellurium, caesium, thallium and antimony each in an amount, calculated as metal oxide, of from 0.01 to 20% by weight, each based on the oxygen-containing compounds and calculated as total amount of metal oxide.

2. A process as claimed in claim 1 wherein the oxidation is carried out with a starting material (I) in whose formula $R^1$, $R^2$ and $R^3$ are identical or different and each is hydrogen or alkyl of one to four carbon atoms and the said radical may bear one or more alkoxy groups or alkyl groups each of one to three carbon atoms as substituents.

3. A process as claimed in claim 1 wherein the oxidation is carried out with a loading of from 5 to 100 grams of starting material (I) per cubic meter (STP) of air.

4. A process as claimed in claim 1 wherein the oxidation is carried out with from 20 to 2000 grams of starting material (I) per liter of catalyst (or supported catalyst) per hour.

5. A process as claimed in claim 1 wherein the oxidation is carried out in the presence of
  a. an oxygen-containing compound of vanadium in an amount, calculated as vanadium pentoxide, of from 5 to 66% by weight;
  b. an oxygen-containing compound of titanium in an amount, calculated as titanium dioxide, of from 40 to 90% by weight; and
  c. one or more oxygen-containing compounds of one or more of the metals tellurium, caesium, thallium or antimony each in an amount, calculated as metal oxide, of from 0.1 to 10% by weight in the case of antimony and tellurium, from 0.1 to 5% by weight in the case of thallium and in the case of caesium of from 0.1 to 5% by weight; each based on the oxygen-containing compounds and calculated as the total amount of metal oxide.

6. A process as claimed in claim 1 wherein the oxidation is carried out with titanium dioxide in the form of anatase.

7. A process as claimed in claim 1 wherein the oxidation is carried out with a catalyst having an internal surface area of from 1 to 80 square meters per gram of catalyst.

8. A process as claimed in claim 1 wherein when a metal oxide such as titanium dioxide is used the oxidation is carried out with particle size of from 0.1 to 1.5 microns.

9. A process as claimed in claim 1 wherein the oxidation is carried out with a supported catalyst having as carrier material: pumice, silicon carbide, silicon oxides, aluminum oxides and/or steatite.

10. A process as claimed in claim 1 wherein the oxidation is carried out with a supported catalyst containing from 0.5 to 30% by weight of catalyst based on the carrier.

11. A process as claimed in claim 1 wherein the oxidation is carried out with a supported catalyst which has a layer of catalyst having a thickness of from 0.02 to 2 millimeters on the carrier.

12. A process as claimed in claim 1 wherein the oxidation is carried out at a temperature of from 200° to 450° C.

13. A process as claimed in claim 1 wherein the oxidation is carried out at a temperature of from 300° to 420° C.

* * * * *